US007279679B2

(12) United States Patent
Old et al.

(10) Patent No.: US 7,279,679 B2
(45) Date of Patent: Oct. 9, 2007

(54) METHODS AND SYSTEMS FOR PEAK DETECTION AND QUANTITATION

(75) Inventors: William M. Old, Boulder, CO (US); Dean R. Thompson, Fort Collins, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 317 days.

(21) Appl. No.: 11/145,459

(22) Filed: Jun. 2, 2005

(65) Prior Publication Data

US 2005/0288872 A1 Dec. 29, 2005

Related U.S. Application Data

(63) Continuation-in-part of application No. 10/603,053, filed on Jun. 24, 2003.

(51) Int. Cl.
*H01J 49/44* (2006.01)
(52) U.S. Cl. ............... 250/282; 702/22; 702/26
(58) Field of Classification Search ............... 250/282; 702/22, 26
See application file for complete search history.

(56) References Cited

U.S. PATENT DOCUMENTS

| 5,247,175 | A | 9/1993 | Schoen et al. |
| 5,470,753 | A | 11/1995 | Sepetov et al. |
| 5,538,897 | A | 7/1996 | Yates, III et al. |
| 5,936,241 | A | 8/1999 | Franzen et al. |
| 6,017,693 | A | 1/2000 | Yates, III et al. |
| 6,051,378 | A | 4/2000 | Monforte et al. |
| 6,104,027 | A | 8/2000 | Gee et al. |
| 6,271,037 | B1 | 8/2001 | Chait et al. |
| 6,931,325 | B2* | 8/2005 | Wall et al. ............ 702/19 |
| 7,075,064 | B2* | 7/2006 | Oliphant et al. ........ 250/281 |
| 7,197,401 | B2* | 3/2007 | Hastings ............ 702/22 |
| 2003/0109990 | A1 | 6/2003 | Axelsson |
| 2004/0096982 | A1 | 5/2004 | Barnea et al. |

FOREIGN PATENT DOCUMENTS

| WO | WO 02/061047 A2 | 8/2002 |
| WO | WO 03/000931 A1 | 3/2003 |

OTHER PUBLICATIONS

Goodlet et al., "Protein Identification with a Single Accurate Mass of a Cysteine-Containing Peptide and Constrained Database Searching," Analytical Chemistry, 72:1112-1118, Mar. 2000.

(Continued)

*Primary Examiner*—David A. Vanore

(57) ABSTRACT

Methods, systems and computer readable media for identifying peaks in a three-dimensional mass spectrometry/elution time dataset. The dataset is represented as a matrix of intensity values with column and row positions corresponding to specific elution time and m/z value, respectively. Peaks may be detected using a watershed image segmentation technique. Further provided are methods, systems and recordable media for creating a mask matrix to be overlaid on a large three-dimensional dataset represented as an image matrix, to identify a much smaller portion of the three dimensional dataset of interest, and to greatly reduce the amount of subsequent processing required for processing data of interest. The mask matrix has the same dimension as the image matrix and includes areas corresponding to one or more peaks identified by the watershed segmentation technique.

29 Claims, 9 Drawing Sheets

OTHER PUBLICATIONS

Horn, et al. "Automated de novo Sequencing of Proteins by Tandem High-Resolution Mass Spectrometry,"PNAS, 97(19):10313-10317, Sep. 2000.

Li, et al. "High-throughput Peptide Identification from Protein Digests Using Data-Dependent Multiplexed Tandem FTICR Mass Spectrometry Coupled with Capillary Liquid Chromatography," Analytical Chemistry, 73:3312-3322, Jul. 2001.

Masselon, et al., Accurate Mass Multipexed Tandem Mass Spectrometry for High-Throughput Polypeptide Identification from Mixtures, Analytical Chemistry, 72:1918-1924, Apr. 2000.

* cited by examiner

METHODS AND SYSTEMS FOR PEAK DETECTION AND QUANTITATION

CROSS REFERENCE TO RELATED APPLICATIONS

This application is a continuation-in-part of co-pending U.S. application Ser. No. 10/603,053, filed on Jun. 24, 2003 and titled "Methods and Devices for Identifying Related Ions from Chromatographic Mass Spectral Datasets Containing Overlapping components", to which we claim priority under 35 U.S.C. Section 120, and which is incorporated herein, in its entirety, by reference thereto.

BACKGROUND OF THE INVENTION

Liquid chromatography/mass spectrometry (LC/MS) is a widely used technique for the global identification and quantitation of proteins and peptides in complex biological samples. In this technique, liquid chromatography is used in-line with a mass spectrometer to chromatographically separate components prior to mass detection, in order to reduce the number of components presented to the mass spectrometer at a given time.

Liquid chromatography is an analytical chromatographic technique that is useful for separating components, typically ions or molecules, that are dissolved in a solvent. In this technique, the components (e.g., analytes) are first dissolved in a solvent and then are forced to flow through a chromatographic column that can range from a few centimeters to several meters. The column is packed with a solid phase chromatographic material that is matched to the solvents in use and binds the analytes via adsorption. An additional, different solvent is then mixed into the flow in increasing concentrations (such as by a smooth gradient increases, or step-wise increases, for example). Each compound in the analyte releases from the solid phase at a specific concentration of the additional solvent and then flows off of the column resulting in a serial separation of the compounds contained in the analyte. A variety of detectors for identifying the presence of compounds in the effluent have been developed over the past thirty years based on a variety of different sensing principles. Typically, signal intensity from a chromatographic detector can be plotted as a function of elution time (a chromatogram) and peaks are used to identify the components. Other techniques, such as characteristic retention time in a chromatographic column, may also be applied to identify the components. A mass spectrometer in this application functions as a very sensitive, multiplexed detector that can detect the presence of multiple compounds simultaneously and can differentiate between the compounds detected.

The evolution of mass spectrometry has been marked by an ever-increasing demand for improved sensitivity, resolution and mass accuracy and a wide variety of different techniques have been used to obtain them. However, at one level, the basic components of all mass spectrometers are essentially the same. These components may be best understood by tracing the ion's path through them. First, an ion source converts the analyte from the liquid (or solid) phase into the gas phase and places a charge on the molecules of the analyte. A common example of an ion source in an LC/MS system is electrospray ionization where the liquid phase input is sprayed into a chamber through a charged needle. Charge is deposited on the surface of the spray droplets and is transferred to the molecules of the analyte during the desolvation process where the solvents are evaporated off. Next, a mass analyzer differentiates the ions according to their mass-to-charge (m/z) ratio. Then, a detector measures the ion beam current to yield an m/z spectrum, where the peaks in the m/z spectrum may be used to differentiate and identify the input components.

A mass spectrometer produces a mass spectrum (m/z versus intensity) integrated over a finite interval of time. In the direct coupling of a liquid chromatography (LC) apparatus with a mass spectrometer (MS), each of these spectra represent an integrated view of the components coming off of the LC column over that interval. The mass spectrometer is typically set to gather a spectrum for a fixed repeating interval (e.g., over a period of five seconds, or some other preset interval). A single spectrum is commonly referred to as a scan and the repetition interval is referred to as the scan rate. The result is a set of ordered, two-dimensional spectra that can be treated as a single, three-dimensional data set, where the X-axis of the three-dimensional space represents elution time, the Y-axis represents m/z values and the Z-axis represents intensity. When using high resolution instruments under conditions where there is a large number of data points in each spectrum or scan, running the instruments at a high scan rate can result in output data sets which are very large and unwieldy (e.g., on the order of one gigabyte and greater).

An important aspect of analyzing LC/MS datasets involves peak detection to identify the ion current associated with each eluting component. As mentioned, peak detection is traditionally performed in a single dimension at a time, either in the chromatographic dimension (a chromatogram), where the intensity at each time point is the sum of the intensities over a given m/z range, or in the mass-to-charge (m/z) dimension (an m/z spectrum), where the intensity at each mass point represents the sum of intensities over a given time range. Peaks identified in this fashion may contain significant quantities of contaminating signal (e.g., from noise or adjacent compounds) and hence this approach to identification typically requires significant knowledge as to the behavior of the components/analytes being studied, to increase the probability that all of the ion current associated with a particular peak is considered when analyzing the same.

Quantitation generally refers to the processing step or steps involved in determining an amount or quantity of molecule rather than identifying a particular type or types of molecules. Quantitation may be performed, at least in part, by integrating the total ion current associated with a particular peak representing the ion of interest. When peak detection is performed in only one dimension, either in elution time using ion chromatograms or in m/z using spectra, the resulting contamination and/or missing ion current can result in significant inaccuracy of the quantitation results.

While two dimensional peak assessment has been attempted with regard to nuclear magnetic resonance (NMR) data analysis, such techniques have not been successful with regard to mass spectrometry/elution time data, as they have not performed well due to the localized nature of noise observed in such datasets, (e.g., LC/MS datasets). As a result, most peak detection methods for LC/MS and other mass spectrometry/elution time datasets continue to be performed in one dimension, either in the m/z (spectral) or elution time (chromatograph) dimensions.

Thus, there is a need to provide a method for peak detection and quantitation of large datasets such as LC/MS datasets and other mass spectrometry/elution time datasets in the elution time and m/z dimensions simultaneously. Such methods may be applicable for the analysis of proteins as well as other classes of molecules sharing similar characteristics.

SUMMARY OF THE INVENTION

Methods, systems and recordable media are provided for identifying peaks in a three-dimensional mass spectrometry/elution time dataset represented as an image matrix. A complement image of the image matrix and the intensity valleys of the complement image are determined. The intensity valleys are then imposed onto the complement image to form a superimposed image. Next, watershed image segmentation is performed on a negative complement of the superimposed image to identify peaks and detect areas of the peaks, in time and mass dimensions.

Further provided are methods, systems and recordable media for creating a mask to be overlaid on a large three-dimensional dataset represented as an image matrix, to identify a much smaller portion of the three dimensional dataset of interest, to greatly reduce the amount of subsequent processing required for processing data of interest. Peak areas of the image matrix in two dimensions are determined using a watershed image segmentation technique. Then, at least one of the peak boundaries is selected, and a mask matrix that has the same dimension as the image matrix is provided. In the mask matrix, a first value is assigned to each location corresponding to identified locations within the at least one selected peak area, while a second value is assigned to each location that does not correspond to a location within the at least one selected peak area.

Methods, systems and recordable media are provided for identifying related ions in a liquid chromatography/mass spectrometry (LC/MS) dataset. Using a watershed image segmentation technique, spectral intensity peaks of the input dataset are detected. Then, for each detected peak, a peak chromatogram is generated by summing extracted ion chromatograms that span the detected peak. The input dataset is a matrix of intensity values with column and row positions corresponding to specific elution time and m/z value. Using the peak chromatograms, a correlation matrix is generated, wherein each element of the correlation matrix is a correlation value and having associated row and column identifiers identifying which peak chromatogram in the input dataset is associated with the correlation value. Subsequently, correlation matrices are clustered.

These and other advantages and features of the present systems, methods and computer readable media will become apparent to those persons skilled in the art upon reading the details as more fully described below.

DETAILED DESCRIPTION OF THE INVENTION

Figure 1:
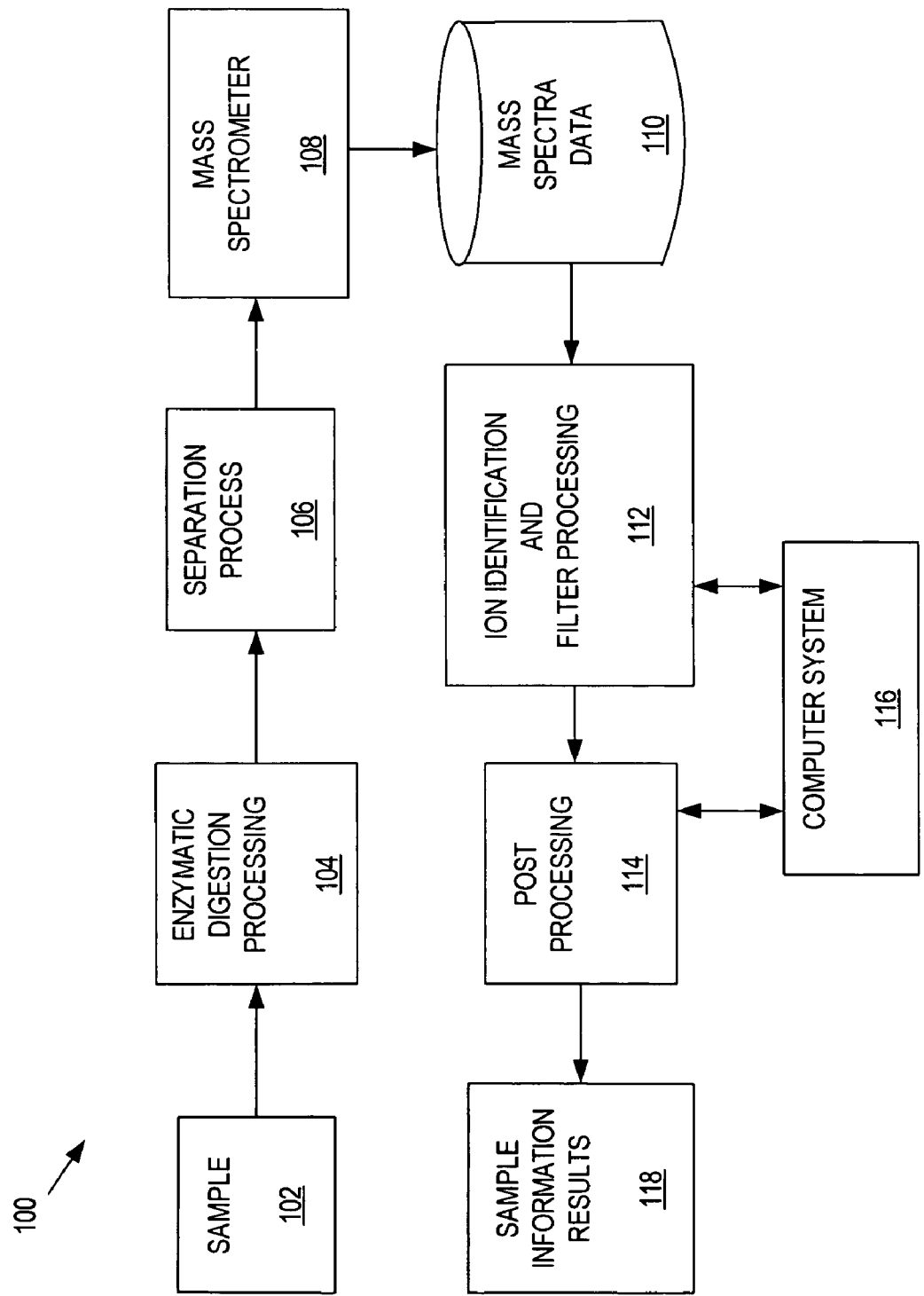
FIG. 1 shows a flow chart illustrating exemplary steps for generating and processing LC/MS datasets for proteins.

Before the present systems and methods are described, it is to be understood that this invention is not limited to particular data, software, hardware or method steps described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a peak" includes a plurality of such peaks and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Definitions

In the present application, unless a contrary intention appears, the following terms refer to the indicated characteristics.

When one item is indicated as being "remote" from another, this is referenced that the two items are at least in different buildings, and may be at least one mile, ten miles, or at least one hundred miles apart.

"Communicating" information references transmitting the data representing that information as electrical signals over a suitable communication channel (for example, a private or public network).

"Forwarding" an item refers to any means of getting that item from one location to the next, whether by physically transporting that item or otherwise (where that is possible)

and includes, at least in the case of data, physically transporting a medium carrying the data or communicating the data.

A "processor" references any hardware and/or software combination that will perform the functions required of it. For example, any processor herein may be a programmable digital microprocessor such as available in the form of a mainframe, server, or personal computer. Where the processor is programmable, suitable programming can be communicated from a remote location to the processor, or previously saved in a computer program product. For example, a magnetic or optical disk may carry the programming, and can be read by a suitable disk reader communicating with each processor at its corresponding station.

Reference to a singular item, includes the possibility that there are plural of the same items present.

"May" means optionally.

Description

In contrast to existing methods for peak detection either in the chromatographic (a chromatogram) or mass-to-charge (m/z) dimension (a m/z spectrum), peak detection in LC/MS datasets in both time and m/z dimensions simultaneously serves several purposes. Firstly, it identifies peaks of interest as inputs for subsequent isotope and charge deconvolution algorithms and peptide identification algorithms. Secondly, it reduces the dataset size by representing the dataset as a list of peaks (m/z, elution time, and integrated intensity). Thirdly, it naturally extends to quantitation by defining the two-dimensional peak boundary over which the signal intensity may be integrated to obtain the peak volume. Accordingly, two-dimensional peak detection methods can be more straightforward and potentially more accurate, especially for quantitation purposes, than the conventional one-dimensional detection methods.

Referring now to FIG. 1, shown is an example of a block diagram 100 of processing steps that may be performed in connection with identification of a molecule within a mixture in a sample. In this particular example, sample or substance 102 may be a mixture of one or more molecules, for example, such as peptides or proteins, being processed for identification. It should be noted that the techniques described herein may also be used in performing a quantitative analysis of molecules in sample 102, including, but not limited to small molecules such as small molecule metabolites, pesticides, etc. Optionally, input sample 102 may be digested by enzymatic digestion processing 104. Enzymatic digestion processing 104 is particular to the processing of proteins and breaks the proteins in sample 102 into shorter polypeptide chains. Enzymatic digestion processing 104 is not typically used when performing analysis of intact proteins or non-protein mixtures, for example. Subsequently, the digests may then be separated via separation processing 106 to reduce the complexity of the mixture presented to the mass spectrometer at a given point in time.

A variety of techniques may be used singly or in combination to perform the separation 106. Whatever techniques are used, separation 106 is performed to isolate as much as practically possible, individual compounds contained in sample 102. The isolation may occur spatially (e.g., different regions on a gel, or different vials from a liquid phase fractionation, etc.) or temporally (e.g., different time points in the flow from an LC column). A typical, although non-limiting example involves the performance of three distinct separations in order. During the first separation, three to five fractions are collected from a size exclusion chromatography column. During the second separation, each of the fractions collected in the first separation is further separated by capturing six to ten fractions from a strong cation exchange (SCX) chromatography column, resulting in a total of eighteen to fifty fractions. During the third separation, each of the fractions resulting from performance of the second separation is injected in turn onto a reverse phase LC column and run with a sixty minute gradient with the outflow of the column being sprayed directly into a mass spectrometer, resulting in eighteen to fifty discrete data sets. In this example, the first two separation steps result in a spatial separation (into different vials) and the last separation results in temporal separation. In such an example, steps 108-118 are repeated for each fraction (vial).

The separation process 106 is particularly useful when the final separation provides a nearly continuous flow as would result from a continuous solvent gradient in an LC system, providing a continuously changing mixture to the mass spectrometer at each point in time. For example, even with relatively simple samples, it may be extremely difficult and time consuming to separate the sample into fractions containing pure compounds. When the input to the mass spectrometer is continuously changing, various techniques may be used to further separate sample 102 into a series of pure compounds, via computational methods, as described previously. Such conditions may result from direct injection to the mass spectrometer from the LC or from LC deposition onto a MALDI (Matrix Assisted Laser Desorption Ionization) surface with in-order processing of the resulting spots or trail.

After separation processing 106, the resulting separations may be input to mass spectrometer 108 producing mass spectra data 110 as an output. Mass spectra data 110 may be input to ion identification and filter processing 112. Ion identification and filter processing 112 may use computer system 116 in connection with performing processing steps therein. Details about the specific processing steps performed in connection with ion identification and filter processing 112 are described elsewhere herein in more detail. Subsequently, output of ion identification and filtering processing 112 may serve as an input to post-processing 114.

Post-processing 114 may include, for example, performing de-isotoping or charge assignment. De-isotoping (or, equivalently isotope deconvolution) and charge assignment may be performed since charge is determined by isotope spacing. Post-processing 114 may also include charge deconvolution that is treated separately. The actual collapsing of isotope peaks into the $C^{12}$ peak or combining the different charge peaks may be performed as an option. Post-processing 114 may further include for example, comparison of monitored output data to known spectral data, for example, in order to identify a particular known type and quantity associated with proteins and the like that may be included in sample 102. Post-processing 114 may also use computer system 116. It should be noted that post-processing 114 may use the same or different computer system used in connection with the processing steps of ion identification and filter processing 112. As an output of post processing, sample information results 118 may be produced. Results 118 may include, for example, types of known proteins and quantities identified in sample 102.

As mentioned, a mass spectrometer may be characterized as an instrument that measures the mass to charge ratios of individual molecules that have been converted into ions. A mass spectrometer does not actually measure the molecular mass directly, but rather determines the mass-to-charge ratio of the ions formed from a particular molecule or molecules.

A useful unit for purposes described herein is a unit referring to a fundamental unit of charge, the magnitude of the charge on a proton. The charge state of an ion may be denoted by the integer number z of the fundamental unit of charge and the mass-to-charge ratio may be referred to as m/z.

Figure 2:
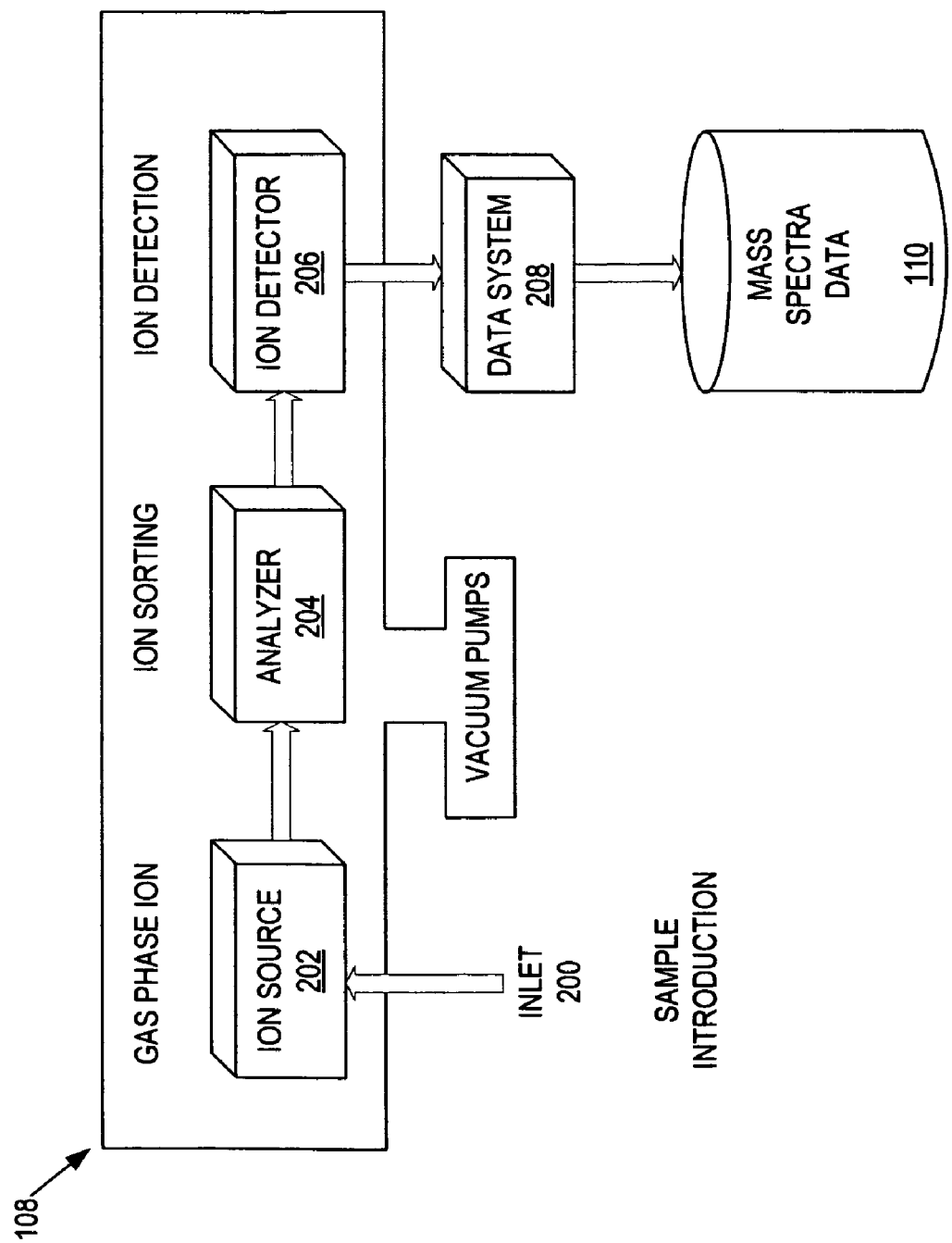
FIG. 2 is an example of a functional block diagram of components included in a mass spectrometer.

FIG. 2 includes the different functional units of a mass spectrometer that may be represented conceptually in block 108 of FIG. 1. A sample may be introduced via an inlet 200 into a vacuum chamber. It should be noted that the sample may be in any one of a variety of different forms including, for example, a liquid solution, embedded in a solid matrix, or a vapor. Depending on the type of inlet and ionization techniques used, the sample may already exist as ions in solution, or it may be ionized in conjunction with its volatilization or by other methods in the ion source 202. Electrospray is one of the most common technique for performing ionization in LC/MS systems, and is an atmospheric pressure process. Molecules are ionized using the electrospray process and are then introduced into the vacuum region. In this embodiment, as the sample from liquid chromatographer 106 is introduced into the inlet 200, the sample is placed in a gas phase and charged to produce ions by ion source 202. The ions are sorted by analyzer 204 according to their mass-to-charge or m/z ratios and then collected by ion detector 206. In ion detector 206, the ion flux may be converted to a proportionate electrical current. Output of ion detector 206 serves as an input to data system 208 recording the magnitude of the various electrical signals as a function of the m/z ratios and converting the information into mass spectra data 110.

It should be noted that in the foregoing general description regarding a mass spectrometer, different types of mass spectrometers may vary from the components included in FIG. 2. For example, the ion sorting described above may be included in a quadrupole instrument but not in a time-of-flight (TOF) mass spectrometer since the TOF mass spectrometer measures the flight time of the ions in a fixed length tube. The techniques described herein may be used with any type of mass spectrometer and any description to a particular type of mass spectrometer should not be construed so as to limit the application of the techniques described herein.

It should be further noted that an embodiment may include ion selection processing as part of ion sorting by analyzer 204 in which only a portion of the particular ions is selected for further processing and analysis. It should be also noted that the ions coming from mass spectrometer 108 may have a net positive or a net negative charge, although for proteomics applications, the ions are typically positively charged.

Molecular and fragment ions may be produced by ion source 202 as shown in FIG. 2. If the input is not already ionized, any one of a variety of different ionization techniques may be used, for example, including electro-spray ionization (ESI). It should be noted that although both positive and negative ions may be generated by ion source 202 at the same time, a single polarity may be recorded at any particular time. A given mass spectrum may include positive or negative ions. The ions are then input to ion sorting or analyzer 204. Analyzer 204 may use dispersion or filtering to sort ions according the mass-to-charge ratios or other relative properties. Typically, analyzers may include for example magnetic sectors, quadrupole mass filters, Fourier transform ion cyclotron resonance spectrometers, time of flight mass analyzers and the like. Subsequently, the sorted ions produced by ion sorter or analyzer 204 are input into ion detector 206 where the particular charge of the ions are determined.

It should be noted that a computer may be used in connection with controlling the mass spectrometer as well as in spectrum acquisition, storage and presentation. As described herein for example in connection with the processing of the block diagram 100 of FIG. 1, software and/or hardware may be used in a computer system in connection with performing quantization, spectral interpretation, and compound identification.

It should be noted that in addition to the ESI technique to generate ions as a result of ion source processing within a mass spectrometer, chemical ionization, desorption ionization, electro spray ionization, and the like may be used in connection with performing ionization. It should be noted that for polypeptides, and the like (biomolecules), techniques such as ESI, Matrix Assisted Laser Desorption Ionization (MALDI), Atmospheric-Pressure MALDI (AP-MALDI), and other "soft" ionization techniques are preferred over "hard" ionization techniques. Soft and hard with respect to ionization techniques refer to the energy levels used to ionize the molecules of interest. Hard ionization techniques are not compatible with biomolecules because they result in extensive fragmentation.

As mentioned in operational block 106, a liquid chromatograph may be used to simplify mass spectra for a sample with multiple compounds by separating the compounds into a series of eluting components. The use of liquid chromatographic techniques may be preferred due to the ease with which they may be interfaced with a mass spectrometer in addition to the ability to monitor the chromatographic behavior of eluting components. A liquid chromatograph may also be used as well as capillary electrophoresis devices and other types of hardware and/or software used in connection with performing the separation processing prior to introduction of a sample into inlet 200.

In connection with LC/MS or other combinations, mass spectra data 110 consists of a series of mass spectra acquired over time. To generate this information, mass spectrometer 108 may scan the mass range, for example, for a particular m/z range repeatedly for a particular chromatographic run. A scan may be taken at a predetermined frequency, such as, for example, every second, or several times a second.

The particular scan frequency selected may vary in accordance with an embodiment. An embodiment may select a scan frequency that varies with the average expected peak width, and the scan frequency may be, for example, an order of magnitude greater than this. In one embodiment, mass spectrometer 108 scans at a rate, which is 10-fold higher than the rate at which compounds are eluting. This translates to at least 10 scans over an average chromatographic peak.

Figure 3A:
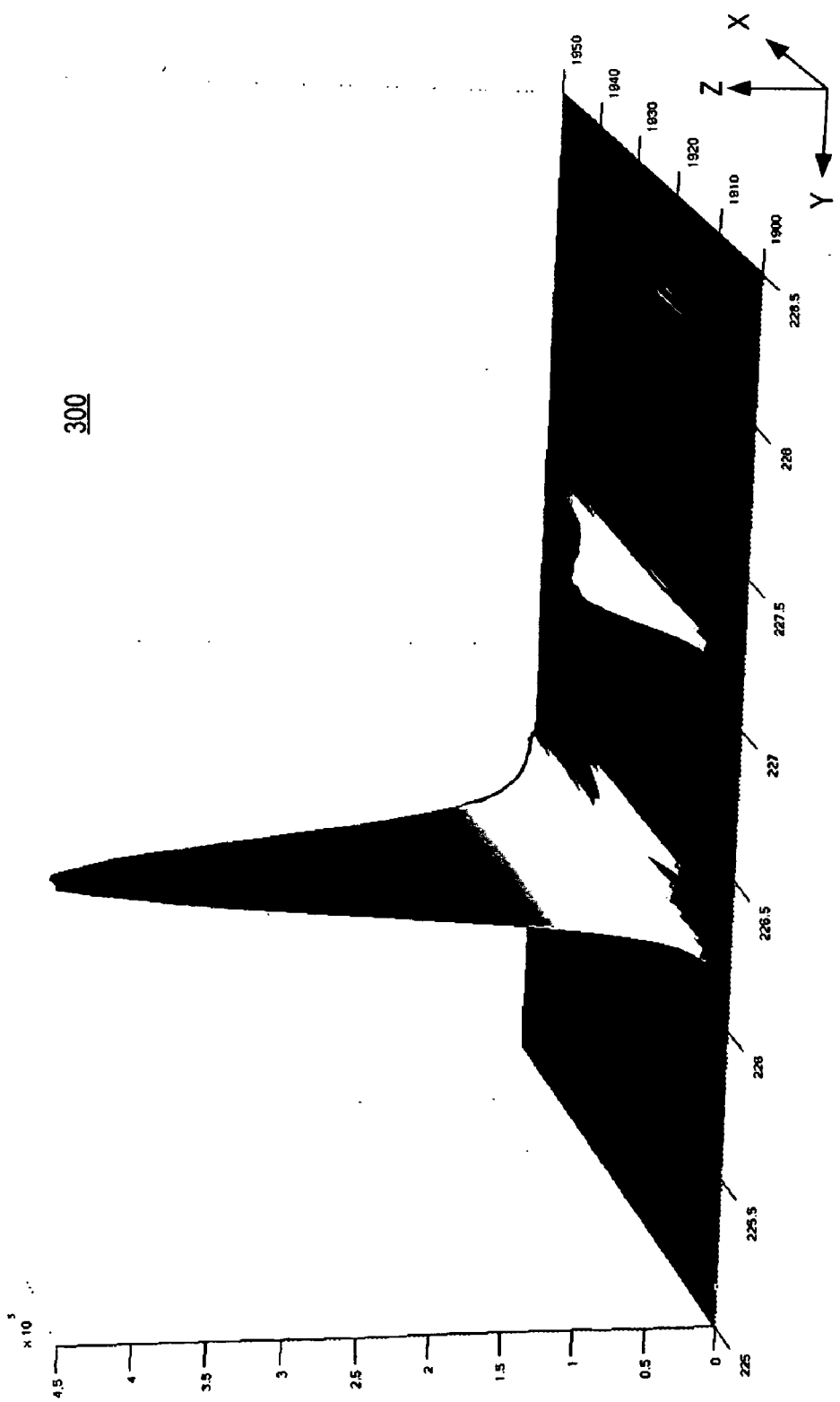
FIG. 3A shows a partial three-dimensional display of a LC/MS dataset output from the data system of the mass spectrometer in FIG. 2.

FIG. 3A shows a three-dimensional dataset 300 output from data system 208 in FIG. 2. Dataset display of a portion of an LC/MS 300 includes a series of mass spectra (y-axis) acquired at increasing elution times (x-axis), which result in a matrix of intensity values (z-axis) with column and row positions corresponding to specific elution time (column position) and m/z value (row position), and intensity, which is the third dimension, that may be also represented by color variation of the data points to represent variation in the intensity values. The "m/z value" is a measurement of ion mass as detected by mass spectrometer 108. The "m/z value" actually corresponds to (m+z)/z, where m is the mass of the ion in Daltons (Da) and z is the charge state of the ion. The m/z value is properly measured in Thompsons, but m/z is a unitless ratio that is commonly used. Thus, for example, an ion with a charge of +2 and a mass of 198 Da gives an "m/z value" of 100 (i.e., (198+2)/2). In this example, the portion of the dataset 300 shown has 50 columns (i.e., 50 scans or spectra at varying elution times, ranging from 1900 to 1950) and 200 rows (m/z values ranging from 225 to 228.5), while intensity ranges up to $4.0 \times 10^5$.

Figure 3B:
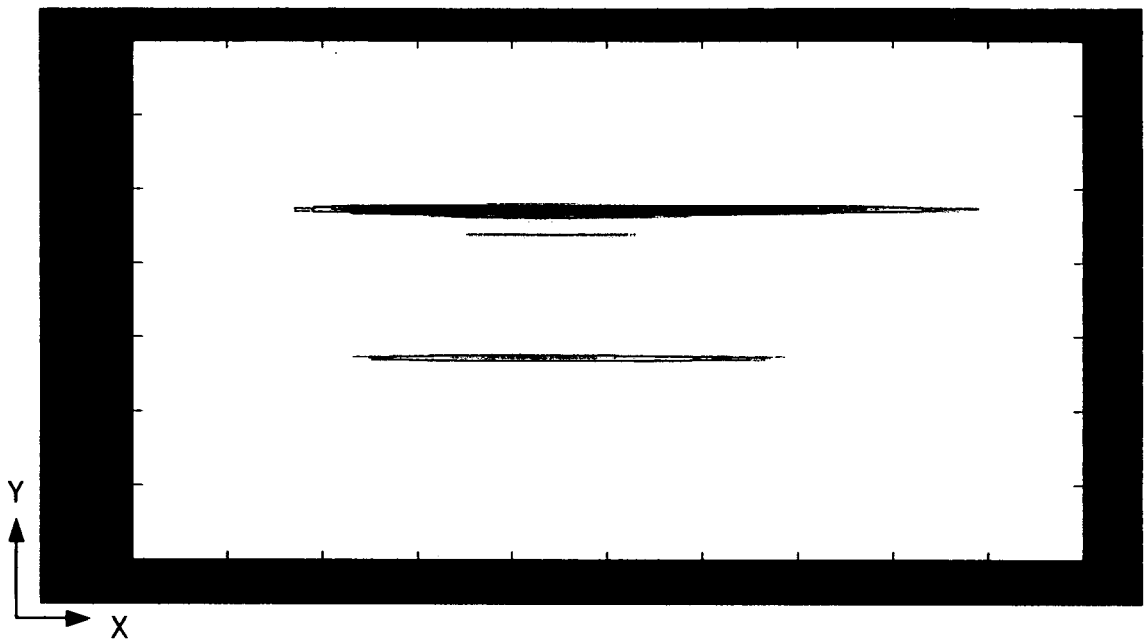
FIG. 3B is a contour plot of the LC/MS dataset in FIG. 3A as an image, illustrating distribution of intensity value in a grey scale.

FIG. 3B is a contour plot of LC/MS dataset 300 as an image, illustrating presentation of intensity distribution in a grey scale. As in FIG. 3A, x- and y-axes represent elution time and m/z value, respectively, while the intensity is represented in grey scale. Viewing a slice vertically through contour plot of FIG. 3B results in a m/z spectrum for a particular elution time. A horizontal slice represents the ion current for a particular m/z value over time, which is commonly referred to as the extracted ion chromatogram (XIC). Conventional grey scale has 256 shades that may not be sufficient to accommodate the full intensity range of LC/MS dataset 300. Thus, the number of shades of grey in FIG. 3B is essentially determined by the maximum intensity in dataset 300, more specifically proportional to the logarithm of the maximum intensity.

As can be noticed from FIGS. 3A-B, the size of LC/MS dataset 300 is proportional to the number of scans as well as number of mass samples in an m/z spectrum. Consider, for example, an embodiment performing analysis of a LC/MS dataset that has 2,500 scans, where each scan has 100,000 mass samples. Such dataset has $2.5 \times 10^8$ intensity values and, at 4 bytes an element, needs a storage capacity of 1 GB.

Figure 4:
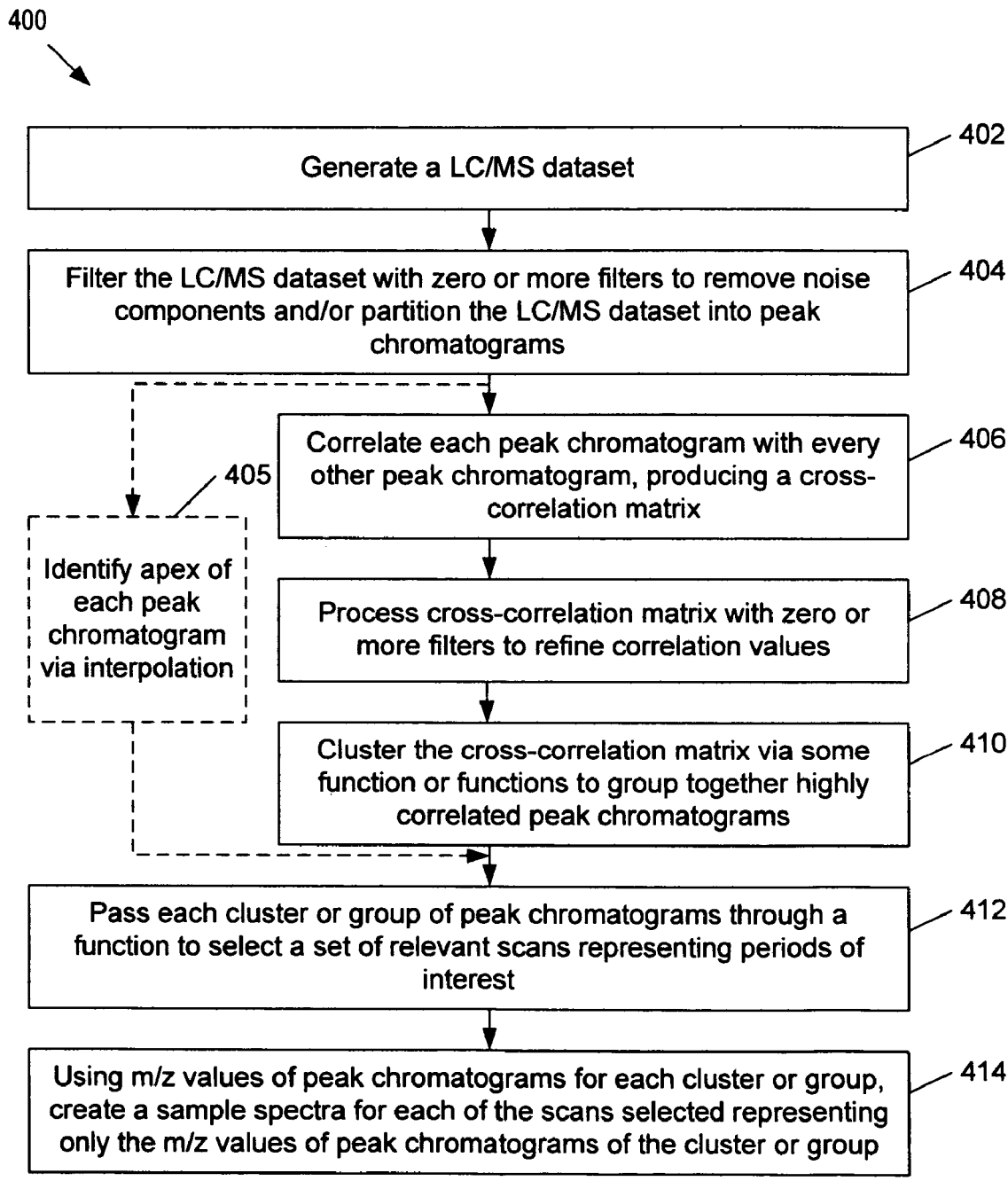
FIG. 4 shows a flow chart illustrating exemplary steps for performing ion identification and filter processing on a LC/MS dataset in accordance with one embodiment of the present teachings.

Referring now to FIG. 4, shown is a flow chart 400 of processing steps that may be included in an embodiment of the ion identification and filter processing 112 previously described in connection with FIG. 1. At step 402, a LC/MS dataset is generated as a result of mass spectrometer processing. The format of the LC/MS dataset used in connection with the processing steps described herein is a two-dimensional matrix having a row index on the Y axis of the m/z ratio, and a column index on the X axis of a scan number. The value within a cell or entry identified by a row and column is the associated intensity value.

At step 404, the data may be filtered with zero or more filters to remove noise components and/or partition the dataset into particular m/z ranges or time periods. It should be noted that in order to reduce the "noise" in the dataset being analyzed, the choice of filters and the particular combination and order used may vary depending on the quality of the data. Various filtering techniques may be found in U.S. patent application Ser. No. 10/603,053, entitled "Methods and Devices for Identifying Related Ions from Chromatographic Mass Spectral Datasets Containing Overlapping Components," which was incorporated by reference above.

The output of the filtering processing of step 404 is a data matrix with the same number of columns (scans or time points) as the original matrix. An embodiment may have a reduced number of rows as a result of step 404 processing in comparison to the number of rows in the original dataset due to removal of the zero rows generated by filtering of noise.

As an alternative, or in addition, to filter processing at step 404, an embodiment may partition the dataset to reduce the number of rows in the data matrix. One embodiment may select only those rows of data within a particular m/z range using detected data peaks of the LC/MS dataset. In this embodiment, data peaks may be determined and a particular m/z range may be selected for a range of values on spanning each data peak. Details of peak detection method will be given later.

Use of partitioning at step 404 refers to a process of data reduction. At some point, partitioning may become necessary because of memory constraints due to the size of the resultant correlation matrix formed and used in other processing steps described elsewhere herein. The size of the correlation matrix depends on the number of rows in the original data matrix (number of non-zero mass samples). Consider, for example, an embodiment performing the processing steps described herein in connection with flow chart 400 using time of flight (TOF) datasets having greater than 100,000 mass samples for each spectrum in the dataset. If all m/z rows of the dataset are considered, assuming that there is no truncation or filtering, then the correlation matrix has 1e10 elements, which at 4 bytes an element, results in a 39 GB matrix.

Referring back to FIGS. 3A-B, LC/MS the portion of the dataset 300 shown has approximately 200 m/z rows. Actual datasets tend to be much larger, but this serves as a good example. Using a two-dimensional peak detection technique, as will be explained later, six major peaks may be discerned. The peaks, which consist of multiple mass rows or chromatograms, may be combined into a single peak chromatogram by summing all of the intensities within the peak boundary in a row-wise manner. The peak chromatograms may then serve as inputs to the grouping algorithm, rather than using every mass row in the dataset. This results in a significant reduction in the number of rows input to the grouping algorithm, and a smaller size of the resultant correlation matrix. Details of the correlation matrix will be given later. Additionally, peak splitting is no longer necessary with this technique, since the peak detection performs this automatically. The raw extracted ion chromatogram (XIC) for a given m/z range may be multimodal since multiple peaks at a given m/z value may occur at different times across the dataset. By identifying the peaks in two dimensions and creating a peak-specific XIC for each peak, the result is a single modal chromatogram for each peak, at least under conditions where the peaks processes are not malformed or incompletely resolved. Furthermore, quantitation may be performed by summing the intensities within the peak boundaries. In the case of LC/MS dataset in FIGS. 3A-B, the dimension of correlation matrix may be 6×6, instead of 200×200.

At step 406, each peak chromatogram may be optionally correlated using some function with every other peak chromatogram producing a correlation matrix representing the degree to which the peak chromatograms are related to one another. The resulting correlation matrix is a two-dimensional matrix symmetrical about the diagonal such that the diagonal entries are 1 and the upper and lower triangular portions are identical. In other words, each entry having indices "i,j" is the same value in the entry having indices "j,i". The correlation for two rows x and y may be represented as:

$$r = \frac{\sum_{i=1}^{n} xi - mx * yi - my}{\sqrt{\sum_{i=1}^{n} (xi - mx)^2} \sqrt{\sum_{i=1}^{n} (yi - my)^2}}$$

in which "mx" represents the mean value of peak chromatogram x, "my" represents the mean value of peak chromatogram y, and the index "i" ranging from 1 to n represents the index of the entry in the peak chromatogram with n being the number of elements in the peak chromatogram.

Alternatively to the cross-correlation processing of steps 406-410, the peaks may be grouped by identifying the apex of each peak chromatogram via interpolation at alternative step 405. The peak groupings are then created by using a function of distance between the centroids (apices) and intensity. A set of seed peaks are identified that represent likely groupings. These peaks may be identified via a variety of mechanisms. For example, a peak may be considered a seed if it has an intensity above a specified threshold and there are not other more intense peaks that have an apex within a given tolerance. Once the set of seed peaks have been identified, other peaks may be grouped with them by a variety of mechanisms. For example, by considering each seed peak in turn and grouping with it other peaks that are not seeds themselves, but have an apex that is closer to the seed being considered than to any other seeds, and have an intensity that is less than the intensity of the seed being considered.

Optionally, at step 408, the correlation matrix may be processed with one or more filters to further refine the correlation values. At step 410, the cross correlation matrix may be clustered using some function or functions to group together highly correlated peak chromatograms or identify clusters of peak chromatograms. Further detailed description regarding clustering or grouping techniques that may be employed may be found in U.S. patent application Ser. No. 10/603,053. An embodiment may also utilize other conventional clustering or grouping techniques such as, for example, hierarchical clustering, K-means clustering and others.

At step 412, each cluster or group of peak chromatograms is passed through a function to select a set of relevant scans representing periods of interest (or, equivalently scans of interest). In one embodiment, the scan corresponding to the maximum point or peak intensity of each peak chromatogram may be determined as a scan of interest. Another embodiment may also determine more than one scan of interest by determining a scan range, for example, utilizing the peak or maximum value. The scans of interest selected may be those scans falling within peak+/−range value, where the range value may vary with an embodiment. The range value may be, for example, ½ the peak value.

One technique for selecting the range of a chromatographic peaks is to select the range that is full width at half maximum (FWHM), meaning that one selects the range between the two points on either side of the peak that are at half the height of the peak. Other embodiments may use other techniques for range determination. As described herein, the scan(s) of interest may vary with embodiment. An embodiment may determine a single point as a scan of interest representing, for example, the maximum average ion signal for the selected peak chromatogram or the time centroid of the cluster. An embodiment may select a range of scans, such as the complete set of scans containing a signal for selected peak chromatograms, and the like. More than one scan may be selected, for example, if the signal is weak and/or there is excessive noise to increase the signal to noise ratio. One technique sums all columns containing a signal for the group to maximize the signal.

At step 414, the m/z values of peak chromatograms for each cluster or group may be used to create a sampled spectrum for each of the scans of interest selected in step 412 representing only the m/z values of the cluster or group. In other words, for each scan value of interest, a corresponding column of intensities from the original LC/MS dataset is used to produce a spectrum for each group. It should be noted that when performing step 414 processing, an embodiment may utilize the original LC/MS dataset or a filtered form of the original dataset to produce the resulting spectra.

As mentioned above, peak detection in datasets having both mass spectrographic scan data and time-elution data (such as LC/MS datasets, for example) may be performed in both time and m/z dimensions simultaneously. Typically, local variations in background intensity of a LC/MS dataset would result in peaks that are close together being merged unless proper account is made for the local variations. Watershed segmentation may be somewhat adaptive to local variation of background intensity in its processing to detect peaks and used as a peak detection method in embodiments of the present teachings. Watershed segmentation starts by partitioning an image into features according to a very low (or very high) grey level threshold that results in the right number of features, where the features may be too small. Then, the threshold is varied to increase the size of the features, but the features are not allowed to merge so that they cannot disappear due to a locally high level of background. However, if there is noise to cause a feature to be incorrectly divided in the first partitioning, or if random noise is identified as a feature, these problems will not be fixed later. To overcome this tendency and to reduce noise without losing weak features in the initial partitioning, several additional processing steps may be employed, such as filtering and/or smoothing, for example, in performing watershed segmentation as described in FIG. 5.

Figure 5:
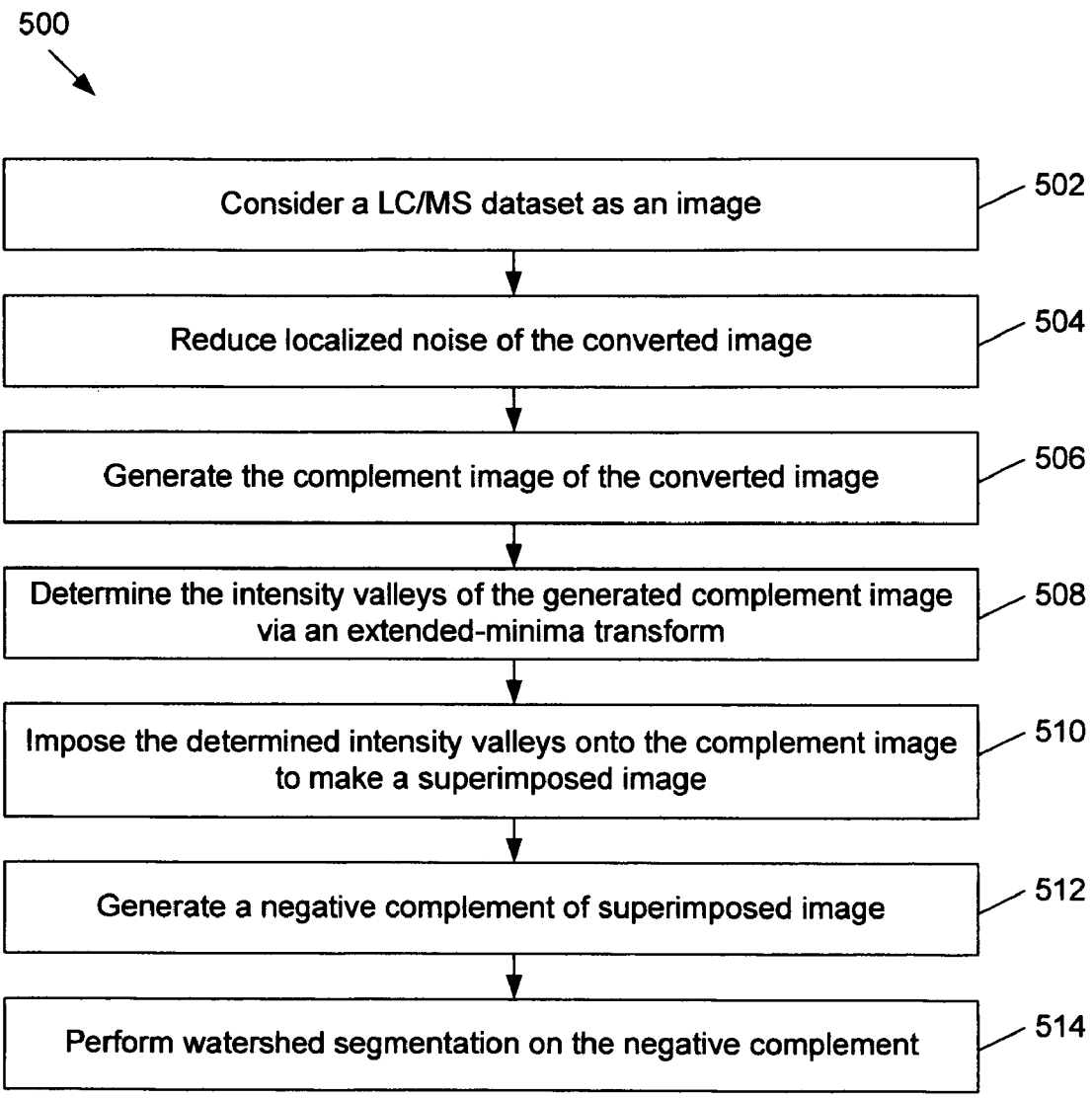
FIG. 5 shows a flow chart illustrating exemplary steps for performing peak detection upon a LC/MS dataset in accordance with one embodiment of the present teachings.

FIG. 5 shows a flow chart 500 illustrating exemplary steps for performing peak detection upon an exemplary LC/MS dataset based on a watershed segmentation technique in accordance with one embodiment of the present teachings. An LC/MS dataset is "converted", treated or considered as an image (image matrix) at step 502. Such consideration involves an interpretation of the dataset such that each cell in the data matrix is considered as (or converted to) a pixel representing the intensity of that cell as a grey scale value.

Then, optionally, at step 504, localized noise in the image may be reduced by subtracting a local baseline estimate on a per flight time bin basis, where noise levels vary typically much more in the flight time (mass) dimension than in the chromatographic time dimension. Also, smoothing of the intensity values may be performed to further reduce the noise. Further optionally, a log transformation may be performed where each element of the image represents a logarithm of the intensity value with column and row positions corresponding to specific elution time (column position) and m/z value (row position). By performing the log transformation on the intensity values, the dynamic range of the image is compressed so that weak features are not lost in the initial partitioning. Alternatively, the log transformation may be carried out prior to the local noise reduction techniques described, or may be carried out even when non-local noise reduction processing is employed. Further alternatively, compression techniques in addition to, or alternative to log transformation may be used to compress the dynamic range of the image, as will be apparent to those of ordinary sill in the art.

Next, the complement of the image is determined at step 506, which essentially inverts the image, i.e., making high values low and low values high. Then, at steps 508 and 510, the intensity valleys of the complement image are determined via an extended-minima transform and superimposed on the complement image as described, for example, in Pierre Soille, "Morphological Image Analysis: Principles and Applications," Springer-Verlag, 1999, pp. 170-171, which is incorporated herein, in its entirety, by reference thereto. Steps 508 and 510 may reduce over-segmentation during subsequent processing steps such as 514, for example.

At step 512, the negative complement of the superimposed image resultant from step 510 is generated. At step 514, watershed segmentation is performed on the negative complement of the superimposed image to detect the peak boundaries (in time and mass) and segments peaks that are not fully resolved. As mentioned, the initial grey level threshold of the watershed segmentation affects the number and size of features, which requires a careful choice of initial threshold. The actual value for the initial threshold may be determined empirically. However, the compression of the data via log transformation, as described, gives more latitude as to the range of values from which the initial threshold value may be chosen. In its simplest form, the initial threshold value may be the minimum intensity of a peak that the user wishes to consider as being above the local background level.

An example of a watershed algorithm that may be used in step 514 is described, for example, in K. R. Castleman, "Digital Image Processing" Prentice-Hall Inc., New Jersey 1996, which is incorporated herein, in its entirety, by reference thereto. One of the existing major applications of watershed algorithm is spot detection in the analysis of two-dimensional gel electrophoresis (2DGE). 2DGE is a method of protein separation, by which proteins in a gel are separated according to the isoelectric point in the horizontal direction (isoelectric focusing [IEF]) and molecular weight in the vertical direction (sodium dodecyl polyacrylamide gel electrophoresis [SDS-PAGE]). After electrophoresis that makes the proteins migrate around the gel, proteins are fixed and are visualized using Coomassie, Silver, and Sypro Ruby stains. Then, the two-dimensional gel containing stained proteins is scanned with a densitometer, where the peaks of the scanned image are processed by watershed algorithm and identified. Typically, an image scanned by a conventional densitometer is represented by 256 grey shades.

One of the major differences between the spot detection and the steps in FIG. 5 is that the watershed algorithm is used at step 514 to find the area each peak covers, where the area may be used as a mask to isolate the mass spectra associated with the peak. Typically, the output of the watershed method is a matrix that has the same dimensionality as the original matrix of LC/MS dataset. Each peak may be numbered and cells in the matrix that are members of a peak contain that peak number. Background (area not part of a given peak) may be assigned to peak 1 (or, equivalently integer 1), while a one-cell wide boundary around each peak may contain zeros, or alternatively, may be included as part of the peak area that the boundary surrounds. From this master matrix, per peak masks can be created (all zeros except for the cells associated with a given peak, which are ones) or a multi-peak mask can be created in the same way.

A mask for a peak (or, equivalently a binary image that defines the area covered by the peak of interest) can be used to isolate and sample out of the mass spectra from the original LC/MS dataset in further analysis. It is noted that peak manipulations described in flowchart 500 would not affect the result of subsequent data processing, since the use of watershed segmentation is only used to create a mask of peak areas that are used to sample the original LC/MS dataset.

It is further noted that watershed processing does not have to be applied to the formation of a mask or masks as described above. Alternatively, a list of peaks identified by the watershed processing may be maintained. For example, for each peak, a list of x-y coordinates of the cells that are members of the peak may be maintained, or stored in a database, RAM, or the like for ready reference thereto. Then, by applying the coordinates of a peak to the dataset, the peak data values of interest can be readily extracted from the large dataset.

Figure 6:
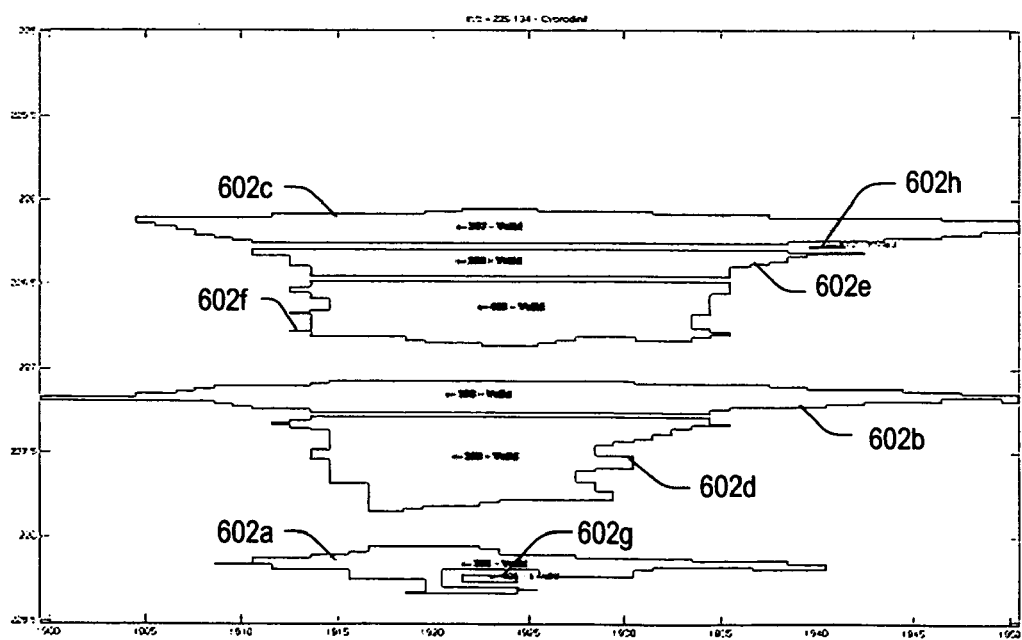
FIG. 6 shows a map of areas covered by peaks that are detected by applying the steps in FIG. 5 to the image in FIG. 3B.

FIG. 6 shows a map of areas covered by peaks that are detected by applying the steps in FIG. 5 to the image in FIG. 3B, where areas 602a-f correspond to the detected peaks P395-P400, respectively. As mentioned, matrix elements of each mask are zeros except those within the area covered by the corresponding peak. For example, the elements of mask matrix for peak P395 are zeros except within area 602a, where the elements within area 602a have a value of 395. Areas 602g-h represent local maxima that were included in the initial segmentation, but which failed other later validity tests related to basic dimensionality of peaks based on an understanding of the nature of the underlying data, which tests are not within the scope of the presently described invention.

By identifying peaks using the watershed technique described above, the area that each peak covers is determined, since peak detection is accomplished in two dimensions simultaneously. Thus, this technique does not need to find a maximum of a peak or a centroid (although these may be determined during processing), but by identifying the area that is considered to cover the range of an identified peak, this area can be mapped out in terms of a mask or template and then used to overlay the entire dataset to sample the data that is contained within the area identified by the mask or template as a peak for further processing. Thus, by creating a matrix from the processing described with regard to FIG. 6, which has the same dimensions as the image matrix of the original dataset, and setting all values in the output matrix to zero except for those occupying the area(s) of one or more identified peak regions (or using some other set of Boolean separation values, i.e. one value assigned to peak regions and a second value assigned to regions not within the areas of the peaks), a mask is created that, when overlaid over the original image matrix, readily separates the data that the researcher is interested in doing further research on from the rest of the data in the vast matrix. Such a mask may be created to identify a single peak area, or to look at multiple peak areas simultaneously.

Thus, the original dataset may be greatly reduced to only the data residing in the identified group of peaks, or may be even further reduced to data residing in one identified peak area, if that is all that the researcher is interested in studying further at the time. This greatly reduces the time and cost of further processing, such as processing of the data by isotope and charge deconvolution algorithms and peptide identification algorithms, for example. Also, by identifying the two-dimensional boundaries of a peak, this process lends itself naturally to facilitating quantification since the signal intensity may be simply integrated over the identified boundaries to obtain the peak volume.

Further, processing such as described with regard to FIG. 5 is advantageously robust in the presence of background and/or chemical noise which may arise from mobile phase clusters and column bleed, for example. Chemical noise and column bleed may result in localized variations in background, where such localized variations may be dealt with in step 504.

Referring back to FIG. 4, the input LC/MS data produced at step 402 may be gathered by running the mass spectrometer at normal energy levels (U spectrum), high fragmentation energy levels (F spectrum), or in alternating scan mode producing alternating U and F spectra. When using alternating scan mode producing datasets including alternating U and F spectra, the chromatographic correlation of the parent peptides (U spectra) and their respective fragment ions (F spectra) may be used to associate parents with their fragments. This characteristic of time or scan correlation between parents and associated fragments may be used, for example, in cases where multiple parents are being fragmented simultaneously, but exhibit sufficient differences in their respective elution profiles. The respective differences in the elution profile enable differentiation between the different parents to be matched with appropriate fragments.

If the input data is produced using the alternating scan mode, two different approaches may be used in processing the input data. In a first approach, the U and F spectra may be combined. In a second alternate approach, the U and F spectra may be processed separately.

For the first approach, the U and corresponding F spectral pairs are added together prior to performing step 406. It should be noted that the F spectrum may be filtered prior to performing the summation of the F and corresponding U spectrum. This filtering may be performed, for example, due to the lower intensity of fragmentation spectra. In one embodiment, a combination of baseline subtraction, Kalman smoothing and Savitzky-Golay filtering are performed. Subsequent to performing the summation, additional filtering may also be performed on the composite spectra. Correlation, filtering, clustering, selection of relevant scans and other processing associated with steps 406, 408, 410, and 412 then proceed as described elsewhere herein resulting in a set of component spectra (U and F combined). In following paragraphs, this may be referred to as the A set. When performing processing associated with step 414, two different spectra are created—one from the original U spectrum at a selected scan for a group, and a second F spectrum sampled at the same scan.

In the first approach, the precursor (parent) ions may be identified by first deriving the A set spectra representing the combined U and F, and then sampling the original U-only dataset at the masses present in set A, and at the scan maximum identified for set A. The parent ions are where there are intensities at the sampled masses in the U-only spectra.

The combined spectra in the A set, assuming that no parents have exactly the same chromatographic profiles, should contain the parent's m/z value with fragments from only that parent. The next step is to determine which m/z value in this A spectrum is the parent. The m/z values identified in the A spectrum are then used to sample the original U spectra at the scan maximum identified for spectrum A. Intensities occurring at these sampled masses in the U spectrum indicate the parent ion masses. Absence of signal at a sampled m/z indicates a fragment ion. By performing the foregoing, the parent masses are identified within the combined U-F component spectrum, spectrum A.

In addition to the first summation approach, a second time correlation approach may be utilized. Correlation processing of step 406 may be performed on the U and F datasets separately. The U and F spectra may be sampled at the scan values as described above in alternating mode. It should be noted that to utilize this second approach, the F spectra should have a sufficient signal to noise ratio for satisfactory correlation. If this is not the case, the summation technique may perform better. Additionally, as with the summation method, filtering techniques may be performed on each of the F and/or U spectra. It should be noted that different filtering techniques may be utilized in an embodiment on the F spectra due to the typical lower signal to noise ratio making the F spectra more error sensitive. As in the summation method, there should be a 1-1 correspondence between the spectra in both the U and F sets, the parents in the sets from the U, and the fragments in the sets from F, correlated in time.

Figure 7:
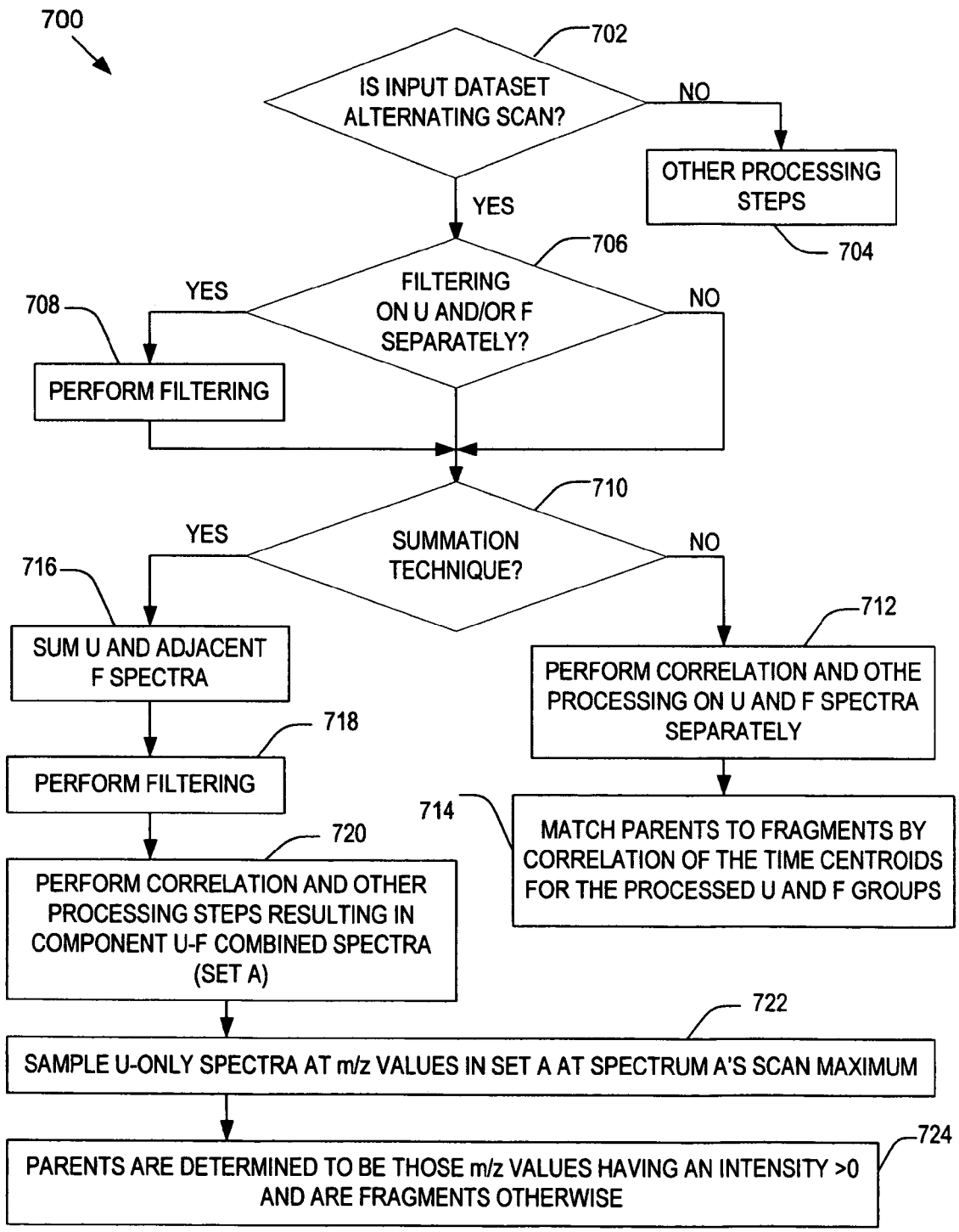
FIG. 7 is a flow chart of method steps of an example embodiment for processing different types of mass spectral datasets.

Referring now to FIG. 7, shown is a flow chart 700 of method steps of one embodiment for performing processing of input spectra produced using a mass spectrometer operating in alternating scan mode. Flow chart 700 summarizes the processing steps described above. At step 702, a determination is made as to whether the input dataset includes alternating U and F spectra. If not, control proceeds to step 704 where the processing steps described in connection with flow chart 400 may be performed to process the input dataset. Otherwise, control proceeds to step 706 where determination is made as to whether any filtering is performed upon the separate U and/or F spectra. If so, control proceeds to step 708 where the filtering is performed prior to step 710. At step 710, a determination is made as to whether the summation technique, the first approach described above, is to be performed. If so, control proceeds to step 716 where U and adjacent F spectra are added together. At step 718, filtering may be optionally performed on the combined U-F spectra. At step 720, the correlation and other processing steps, such as 406, 408, 410, 412 and 414 described in flow chart 400, are performed producing a resultant combined U-F spectra referred to as set A. At step 722, the m/z values identified in the A spectrum are then used to sample the original U spectra at the scan maximum identified for the spectrum in set A. At step 724, parent ion m/z values are determined to be those having an intensity value>0. Absence of a signal at a sampled m/z value such that the intensity=0, indicates a fragment ion.

If at step 710 if it is determined that the summation technique is not used, the alternative second approach, the time correlation approach, is utilized. At step 712, correlation and other processing steps, such as 406, 408, 410, 412 and 414 described in flow chart 400, are performed separately on the U and F spectra. At step 714, the parents are matched to corresponding fragments utilizing the correlation of time centroids for the processed U and F groups.

It should be noted that the mass spectrometer in alternating scan mode may utilize a scan rate that is much higher than the rate at which components are eluting. For example, in one embodiment, the scanning rate is a factor of 10 or more than the rate at which components are eluting from the mass spectrometer. Selected scanning rates are described elsewhere herein.

Figure 8:
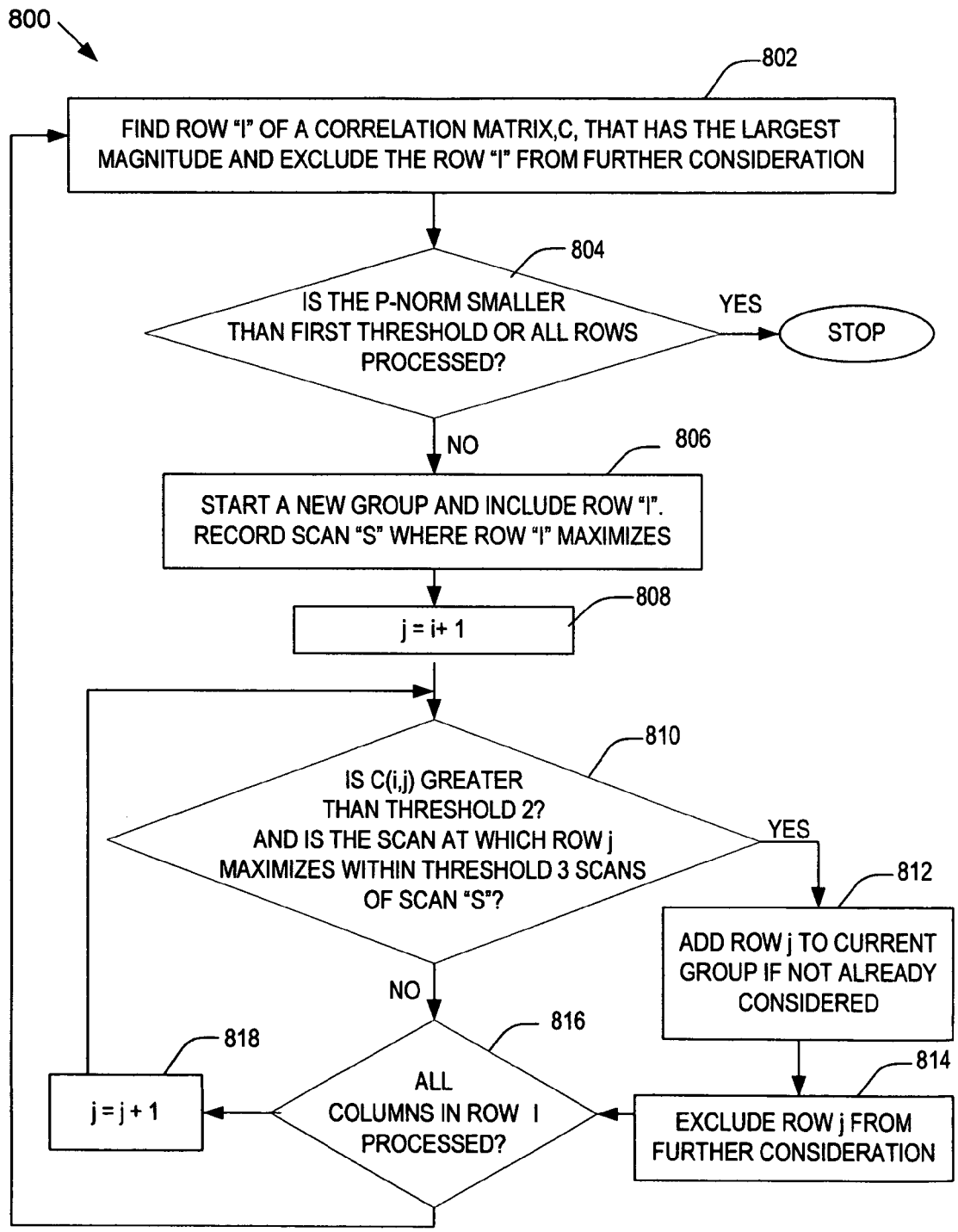
FIG. 8 shows a flow chart illustrating exemplary steps for clustering or grouping of correlation matrix elements in accordance with one embodiment of the present teachings.

If the input dataset includes only U spectra with no fragments, the analysis is performed to examine each peptide in the mixture, or molecule in the sample. Each group corresponds to the charge states and isotopes of a single peptide or molecule co-eluting at the same time. When the input dataset includes only U spectra, the techniques described herein may be used to determine which m/z ratios of peaks are of the same peptide or molecule. This may be a useful preprocessing step prior to performing, for example, charge assignment, isotope clustering, de novo sequencing, database searching, and the like. If the input dataset includes only F spectra, each group corresponds to the charge states, isotopes, and fragments of a single peptide or molecule co-eluting at the same time Referring now to FIG. 8, shown is a flow chart 800 of method steps of an example embodiment of a clustering or grouping process. The method steps of flow chart 800 may be performed as part of step 410 in FIG. 4. The input at step 802 is a correlation matrix, C, produced as a result of step 406 processing. At step 802, the row "i" of the matrix C is determined as the row with the largest magnitude. The magnitude of a vector may be defined in different ways. For example, in one embodiment, the magnitude may be defined as a p-norm of a vector for 1<=p<=infinity, p being an integer value, for a vector $x_1$ as $$\|x\|_p = \left[\sum_{j=1}^{n} |x_j|^p\right]^{\frac{1}{p}}$$

The vector x may include "n" values that are each real or complex elements. In the instance where p=infinity, the following is true.

$$\|x\|_\infty = \max_{1 \le j \le n} |x_j|$$

An embodiment may also use other types of norms in determining a magnitude, such as, for example, other norms involving derivatives, such as the Sobelev norm. Other measures of magnitude that may be included in an embodiment include: a number of elements above a threshold, entropy, concentration, logarithm of energy, and the like.

At step 804, a determination is made as to whether the magnitude is less than a first threshold, or if all rows have been processed. If either condition is true, processing stops. Otherwise, control proceeds to step 806 where a new group is started with the selected row "i" included in the new group. Scan "S" at which row "i" maximizes is also determined and used as a criterion for grouping subsequent rows. The first threshold may vary with each embodiment and may be empirically determined in accordance with each particular dataset and mass spectrometer settings and characteristics. For example, in one embodiment the first threshold may be 0.15 specifying a minimum correlation value. If this first threshold is increased, the number of groups may decrease. At step 808, a counter "j" is initialized to be the value of "i+1". At step 810, a determination is made as to whether the current element, C(i,j) is greater than a second threshold, and whether the peak of row "j" is within a certain number of scans (threshold 3) of scan "S" (peak scan for row "i"). For example, in one embodiment, this second threshold may be 0.75 and the third threshold=2 scans. If C(i,j) is greater than the threshold 2, and the scan difference is less than threshold 3, control proceeds to step 812 where row j is added to the current group if the row j has not already been considered. At step 814, row j is excluded from further consideration and control proceeds to step 816. If, at step 810, it is determined that C(i,j) is not greater than the second threshold, control proceeds directly to step 816.

It should be noted that the selection of the first threshold (threshold 1), as used at step 804, and the second threshold (threshold 2) as used in step 810 may be selected to improve the quality of the groupings of the rows and to minimize the number of ungrouped rows. Threshold 1 may be lowered to minimize the number of ungrouped rows, and threshold 2 may be increased to improve the quality of the grouping. Since selection of these two thresholds is interdependent, the value selected for one varies with the other in an embodiment. It should be noted that the selection of threshold 3 may vary with each embodiment and may be characterized as being data-dependent. For example, selection of threshold 3 may be made depending on the scanning resolution, i.e. how many scans are acquired across a chromatographic peak.

At step 816, a determination is made as to whether all the columns in row "i" have been processed. If not, control proceeds to step 818 where j is increased by 1 and control proceeds to step 810 to examine the next element in the current row. If all columns in row "i" have been processed, control proceeds to step 802 where the next row "i" is determined.

It should be noted that the first threshold described above in connection with step 804 may affect the number of rows of the correlation matrix, which are not included in a group. The ungrouped rows may include, for example, noise, or individual peaks, so that raising the cutoff threshold 1 reduces the number of grouped rows and removes noise in the dataset prior to correlation. Using the example embodiment of clustering or grouping described in connection with FIG. 8, the first and second thresholds in the grouping or clustering processing affect the number of ungrouped rows. Threshold 1 and threshold 2 both vary between 0 and 1. The first threshold, threshold 1, is the threshold for choosing a row as having valid data, and the second threshold, threshold 2, is the threshold for grouping one row with another. Threshold 3 is the maximum separation (in scans or seconds) allowed between a row's chromatographic peak and the seed row's chromatographic peak.

The foregoing processing techniques described herein, for example, in connection with flow chart 400, may not be used in instances where there are two or more molecules that elute at the same time and also have the same elution profile. In this instance, the foregoing processing steps are not able to identify the different peptides and properly pair parent (U spectra) with fragments (F spectra), and another processing technique may be used, for example, as described in U.S. patent application Ser. No. 10/388,088, filed Mar. 13, 2003, entitled "Methods and Devices for Identifying Biopolymers Using Mass Spectroscopy", hereinafter referred to as "the Thompson and Fischer disclosure", which is hereby incorporated herein, in its entirety, by reference thereto. The processing steps of Thompson and Fischer may be performed on the results produced by processing steps described herein to resolve the parent-fragment pairings in instances where two or more molecules elute at the same time. The Thompson and Fischer disclosure describes a method for gathering structural information for biopolymers in a sample by running the mass spectrometer in the alternating scan mode, as described elsewhere herein, with alternating U and F spectra. Alternating scan mode provides for taking a first spectrum (U spectrum) at normal energy levels, such that fragmentation is not induced, and then a next second scan is taken at high fragmentation energy levels (F spectrum) where energy is injected by increased voltage differential between components of the ionization source, frequency stimulation, or some other technique producing a sequence of alternating spectra that can be deconvolved or decomposed to associate the appropriate fragment ions from the F spectrum with the proper parent in the U spectrum. When using an input LC/MS dataset that includes alternating scan mode data, the technique described herein may be a preprocessing step performed prior to the method described in the Thompson and Fischer disclosure to associate the proper parent with the fragments (pairings of U and F spectra). Charge assignment, isotope clustering, de novo sequencing, database searching, and the like may subsequently be performed.

A U spectrum includes peaks that correspond to some and preferably all of the polypeptides in the sample when these polypeptides are unfragmented. A U spectrum may be obtained by detecting the polypeptides in the sample without exposing them to a fragmentation mechanism. It is to be understood that a U spectrum may, in certain embodiments, include peaks that represent fragments of these polypeptides, e.g., fragments that were inadvertently created as a consequence of the mechanism used to ionize and/or detect the polypeptides in the spectrometer.

An F spectrum includes peaks that correspond to a collection of fragments of some and preferably all of the polypeptides in the sample. An F spectrum may be obtained by detecting the polypeptides in the sample after these have been exposed to one or more fragmentation mechanisms. It is to be understood that an F spectrum may, in certain embodiments, include peaks that represent unfragmented polypeptides, e.g., polypeptides that survive exposure to the fragmentation mechanism. It will be appreciated that such situations are most likely to occur when the polypeptides are exposed to relatively low fragmentation energies.

The processing techniques described herein may also be performed using input LC/MS datasets with multimodal chromatograms characterized as ions or sets of ions of the same m/z value but having different chemical compositions. A multimodal curve has multiple peaks rather than a single peak. Multimodal peaks may be detected by applying the steps of flow chart 500. In connection with step 414 processing to produce a resultant spectra, the original LC/MS dataset is again utilized. In particular, as described elsewhere herein, the appropriate columns of intensities for the selected scans are obtained from the original dataset. With multimodal data, it should be noted that an m/z range may appear in more than one group.

An embodiment may utilize any one of different types of mass spectra that may be produced, for example, by a time-of-flight (TOF) mass spectrometer. An example embodiment may include a step following step 402 in which input datasets are converted to a more compact form prior to be used with the foregoing processing steps. For example, a TOF dataset may be converted to be utilized with the foregoing techniques. The TOF input dataset may be a 2-dimensional matrix with the Y-axis indicating the time of flight correlating directly to the m/z values and the elution time on the x-axis. Each column of the TOF data is a scan of the mass spectrum data. This matrix may be converted into a sparser form to minimize storage. The compaction technique used on the matrix may vary in accordance with the functionality and particular components included in each embodiment. One example embodiment utilizes a MATLAB function to compress the matrix into a sparse matrix format. Any needed subsequent conversions may be performed by MATLAB. An embodiment may optionally use other formats depending on memory constraints and other characteristics of an embodiment.

An embodiment may utilize filtering techniques to reduce noise and eliminate data associated with known contaminants. For example, particular correlation values of a known contaminant within a certain m/z range may be eliminated at step 408. Consider, for example, that a known detergent contaminant may be present. The contaminant presence may be determined by manually examining a contour plot and visually locating a constant horizontal band present at all elution times. Input datasets may be examined to automatically test for known contaminants and accordingly remove the bands of data. It should be noted that an example embodiment may provides for "noise" to be filtered that is highly correlated, such as a known contaminant, and/or weakly correlated, such as interference.

It should be noted that the techniques described herein may be used for performing a quantitative analysis rather than for identification processing, for example, such as identifying matching F and U spectra. This may affect the previously described processing steps. When performing a quantitative analysis using the foregoing techniques, points of interest selected, as at step 412, may include those sampled frequently across each group, rather than determining a single maximum as described herein. As described elsewhere herein, step 414 processing produces a single spectra for each ion with contaminants and other co-varying spectra removed. For quantitative analysis using the foregoing techniques, a spectrum is produced for each cluster or group. For quantitation, the peak areas are integrated for the group chromatograms or rows. This provides a group peak area that may be used for relative quantitation with other groups in the dataset. For quantitation, each cluster or group using the foregoing techniques represents a range of m/z values and elution time that contains related signal.

The foregoing provides techniques utilizing the fact that certain groupings tend to co-vary. Parent and related ion fragments tend to co-vary and exhibit similar co-elution profiles. Input data including only U spectra, when processed by the techniques described herein, may be used to group charge states and isotopes of single peptides since these charge states and isotopes co-vary by co-eluting at the same time. Input data including only F spectra may be used to group charge state, isotopes and fragments that co-elute at the same time. The foregoing may also be used as a preprocessing step in connection with the Thompson and Fischer disclosure and other existing processing techniques to identify U and related F spectra when two parent or U spectra within a group have the same elution profile and co-elute at the same time. Such other existing techniques may include, for example, identification algorithms, such as SEQUEST, MASCOT, MSFIT, and the like.

The Thompson and Fischer method and/or other technique may be used to distinguish between two unrelated components (not isotopes, charge states or fragments) that co-elute and exactly co-vary since the techniques described herein will not be able to distinguish between two such unrelated compounds. Different techniques may be used to determine the existence of such a condition indicating a need to invoke alternative techniques to assign these parents to their corresponding fragments. An embodiment may test extracted U spectra for the presence of multiple parents that the foregoing techniques cannot distinguish between as follows. De-isotoping and charge deconvolution may be performed on the spectrum resulting in a neutral mass spectrum (not m/z). The multiple isotopic distributions for each charge state of a single peptide or component may be collapsed into a single mass peak. Thus, if two peptides or components are present in an extracted U spectrum, this deconvolution procedure results in two mass peaks indicating the need to invoke additional processing, such as the Thompson and Fischer method, to match each parent with associated fragment ions.

The foregoing provides techniques for analyzing the chromatographic information of a dataset, such as an LC/MS dataset to separate related ions into spectra representing individual compounds and identifying the specific spectra that provide maximum signal levels for subsequent analysis. Additionally, the foregoing removes noise from the dataset since noise does not tend to co-vary with the real data signals. Constant signals resulting from contaminants may also tend not to co-vary with the real data signals and may also drop out. Since noise is removed using the foregoing techniques in addition to any specific filtering techniques applied, for example, at step 404, performance of subsequent processing, such as de novo sequencing, may be significantly improved. The foregoing also may result in a reduction in the size and complexity of an input dataset used in subsequent processing. The foregoing techniques may be used in protein identification, but may also be applied to other classes of molecules sharing similar characteristics such as, for example, polynucleotides, polysaccharides and other small molecules.

Figure 9:
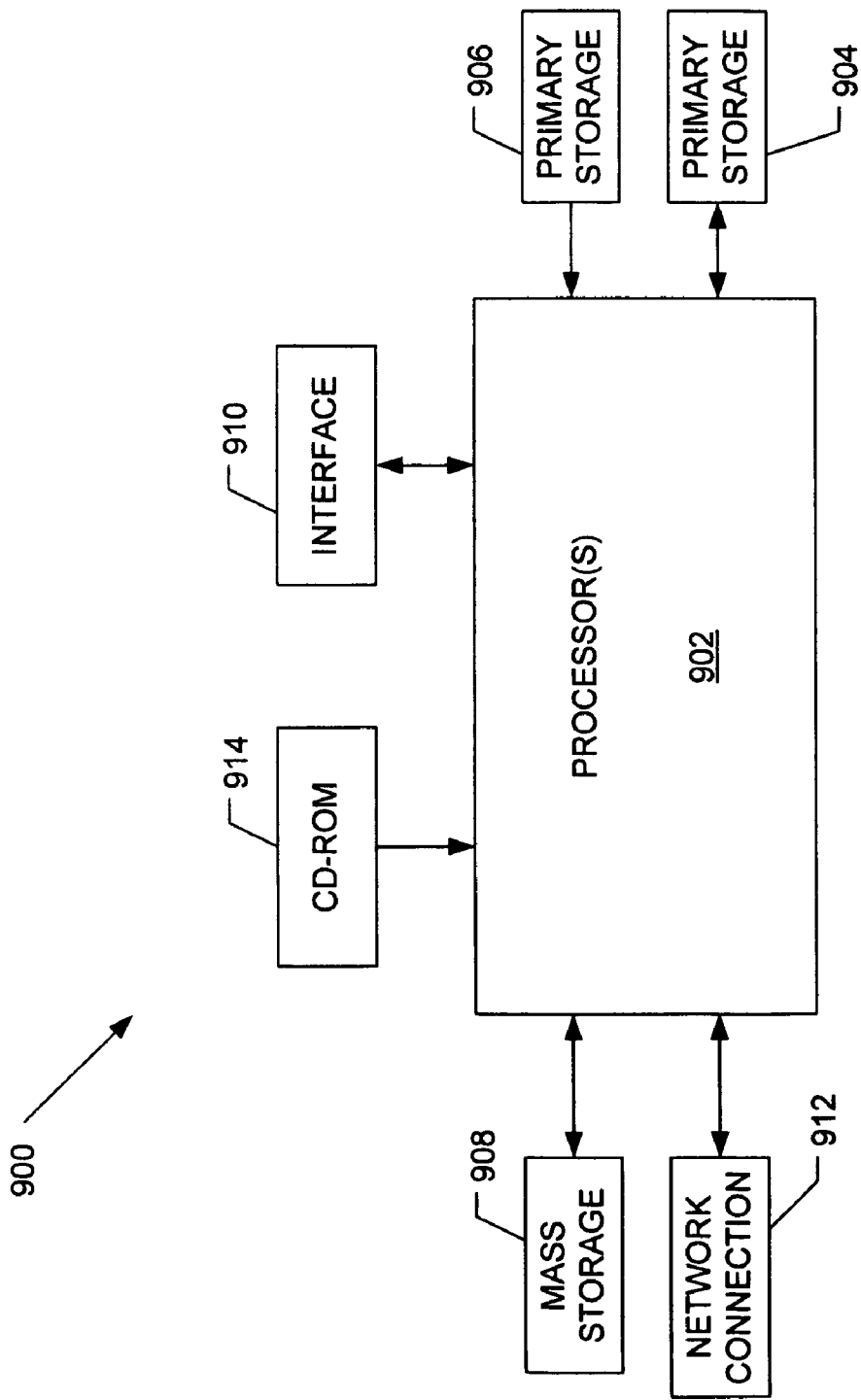
FIG. 9 illustrates a typical computer system that may be employed in accordance with one embodiment of the present invention.

FIG. 9 illustrates a typical computer system in accordance with an embodiment of the present invention. The computer system 900 may include any number of processors 902 (also referred to as central processing units, or CPUs) that are coupled to storage devices including the first primary storage 904 (typically a random access memory, or RAM), and the second primary storage 906 (typically a read only memory, or ROM). As is well known in the art, the first primary storage 904 acts to transfer data and instructions uni-directionally to the CPU and the second primary storage 906 is used typically to transfer data and instructions in a bi-directional manner. Both of these primary storage devices may include any suitable computer-readable media such as those described above. A mass storage device 908 is also coupled bi-directionally to CPU 902 and provides additional data storage capacity and may include any of the computer-readable media described above. Mass storage device 908 may be used to store programs, data and the like and is typically a secondary storage medium such as a hard disk that is slower than primary storage. It will be appreciated that the information retained within the mass storage device 908, may, in appropriate cases, be incorporated in standard fashion as part of primary storage 906 as virtual memory. A specific mass storage device such as a CD-ROM 914 may also pass data uni-directionally to the CPU.

CPU 902 is also coupled to an interface 910 that includes one or more input/output devices such as such as video monitors, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPU 902 optionally may be coupled to a computer or telecommunications network using a network connection as shown generally at 912. With such a network connection, it is contemplated that the CPU might receive information from the network, or might output information to the network in the course of performing the above-described method steps. The above-described devices and materials will be familiar to those of skill in the computer hardware and software arts.

The hardware elements described above may implement the instructions of multiple software modules for performing the operations of this invention. For example, instructions for population of stencils may be stored on mass storage device 908 or 914 and executed on CPU 902 in conjunction with primary memory 906.

In addition, embodiments of the present invention further relate to computer readable media or computer program products that include program instructions and/or data (including data structures) for performing various computer-implemented operations. The media and program instructions may be those specially designed and constructed for the purposes of the present invention, or they may be of the kind well known and available to those having skill in the computer software arts. Examples of computer-readable media include, but are not limited to, magnetic media such as hard disks, floppy disks, and magnetic tape; optical media such as CD-ROM, CDRW, DVD-ROM, or DVD-RW disks; magneto-optical media such as floppy disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, hardware element, process, process step or steps, to the objective, spirit and scope of the present invention. All such modifications are intended to be within the scope of the claims appended hereto.

What is claimed is:

1. A method of identifying peaks in a three-dimensional mass spectrometry/elution time dataset, said method comprising the steps of:
   providing an image matrix of the three dimensional dataset;
   determining a complement image of the image matrix;
   determining intensity valleys of the complement image;
   imposing the intensity valleys onto the complement image to form a superimposed image;
   determining a negative complement of the superimposed image; and
   performing watershed image segmentation on the negative complement of the superimposed image thereby detecting the peak areas, in time and mass dimensions.

2. The method of claim 1, further comprising reducing localized noise of the image matrix prior to said determining a complement image.

3. The method of claim 2, wherein said step of reducing localized noise includes estimating a local baseline per m/z value; and subtracting the estimated local baseline from intensity values of the image matrix.

4. The method of claim 2, further comprising smoothing the intensity values of the image matrix.

5. The method of claim 1, further comprising compressing dynamic range of the image matrix prior to said determining a complement image.

6. The method of claim 5, wherein said compressing dynamic range comprises performing a log transformation on intensity values of the image matrix.

7. The method of claim 1, wherein said performing watershed image segmentation also segments peaks that are not fully resolved.

8. The method of claim 1, wherein said determining the intensity valleys determines local maxima of the image matrix using an extended-minima transform.

9. The method of claim 1, wherein the three dimensional dataset is an LC/MS dataset.

10. The method of claim 1, wherein the three dimensional dataset is produced using electrospray ionization.

11. The method of claim 1, wherein the three dimensional dataset is derived from deposition of output from an LC separation onto a MALDI surface.

12. The method of claim 11, wherein the dataset is deposited onto the MALDI surface as a continuous stripe.

13. The method of claim 11, wherein the dataset is deposited onto the MALDI surface as a series of discrete spots to be processed in order by a MALDI ionization interface of a mass spectrometer.

14. The method of claim 1, further comprising:
creating a mask based on selecting a set of at least one peak area identifying at least one of the identified peaks; and
overlaying the mask on the dataset to identify data to be further processed.

15. The method of claim 14, wherein said creating a mask comprises:
selecting a set of at least one peak area identifying at least one of the identified peaks;
generating a mask matrix having the same dimensions as said image matrix;
assigning values to locations in the mask matrix corresponding to identified locations within the at least one peak area;
assigning a first value to each of the locations in the mask matrix corresponding to locations in the at least one selected peak area; and
assigning a second value to all other locations in the mask matrix which have not already been assigned the first value.

16. The method of claim 15, wherein the first value is one and the second value is zero.

17. The method of claim 15, further comprising further processing the selected data, wherein said processing includes at least one of: processing by isotope and charge deconvolution algorithms; processing by charge deconvolution algorithm; processing by at least one peptide identification algorithm; and quantification processing.

18. The method of claim 14, further comprising selecting the data in the image matrix identified by said overlaying the mask on the image matrix.

19. The method of claim 1, further comprising:
creating a list of peaks, wherein each peak in the list is identified by x-y coordinates of all locations on the image matrix that are members of the respective identified peak.

20. The method of claim 19, further comprising, selecting at least one peak from the list of peaks, and applying the x-y coordinates from each selected peak to the three-dimensional mass spectrometry/elution time dataset to identify data to be further analyzed.

21. A method comprising at least one of transmitting and receiving a result obtained from the method of claim 1.

22. A method for identifying related ions in a liquid chromatography/mass spectrometry (LC/MS) dataset, comprising:
generating a plurality of peak chromatograms from an input LC/MS dataset using the peak areas detected in claim 1, said input dataset being a matrix of intensity values with column and row positions corresponding to specific elution time and m/z value, respectively;
correlating each of the plurality of peak chromatograms with every other of the plurality of peak chromatograms producing a correlation matrix, each element of said correlation matrix including a correlation value and having associated row and column identifiers identifying which peak chromatogram in said input dataset are associated with said correlation value;
clustering said correlation matrix identifying at least one group and at least one row of said correlation matrix as being in said at least one group, each group representing co-varying peak chromatograms;
selecting at least one time period of interest for each group; and
producing a resultant spectrum for each group by sampling extracted ion chromatograms included in each of said groups at each of said at least one time period of interest from said input dataset.

23. The method of claim 22, wherein the step of generating a plurality of peak chromatograms includes the steps of:
determining a plurality of peaks defined by the peak areas detected in claim 1;
composing a peak chromatogram with regard to each of the plurality of peaks by summing extracted ion chromatograms only in columns of each ion chromatogram that span each of the plurality of detected peaks in row-wise manner.

24. A computer readable medium carrying one or more sequences of instructions for identifying peaks in a three-dimensional mass spectrometry/elution time dataset, wherein execution of one or more sequences of instructions by one or more processors causes the one or more processors to perform the steps of:
providing an image matrix of the three dimensional dataset;
determining a complement image of the image matrix;
determining intensity valleys of the complement image;
imposing the intensity valleys onto the complement image to form a superimposed image;
determining a negative complement of the superimposed image; and
performing watershed image segmentation on the negative complement of the superimposed image thereby detecting the peak areas, in time and mass dimensions.

25. A method of creating a mask to be overlaid on a large three-dimensional dataset, to identify a much smaller portion of the three dimensional dataset of interest, said method comprising the steps of:
providing an image matrix of the three dimensional dataset;
determining peak areas of the three dimensional dataset in two dimensions, based on a watershed image segmentation algorithm;
selecting at least one of the determined peak areas;
generating a mask matrix having the same dimensions as said image matrix;
assigning a first value to each of the locations in the mask matrix corresponding to identified locations within the at least one selected peak areas; and
assigning a second value to all locations in the mask matrix which have not already been assigned the first value.

26. The method of claim 25, wherein the large three-dimensional dataset comprises a dataset of intensity values over mass spectrometry/elution time axes.

27. The method of claim 25, wherein the large three-dimensional dataset is an LC/MS dataset.

28. The method of claim 25, wherein said determining peak areas of the three dimensional dataset in two dimensions, based on a watershed image segmentation algorithm comprises:
determining a complement image of the image matrix;
determining intensity valleys of the complement image;
imposing the intensity valleys onto the complement image to form a superimposed image;
determining a negative complement of the superimposed image; and
performing watershed image segmentation on the negative complement of the superimposed image thereby detecting the peak boundaries, in first and second dimensions.

29. A system for identifying related ions in a liquid chromatography/mass spectrometry (LC/MS) dataset, the system comprising:

means for generating a plurality of peak chromatograms from an input LC/MS dataset, said input dataset being a matrix of intensity values with column and row positions corresponding to specific elution time and m/z value, respectively;

means for correlating each of the plurality of peak chromatograms with every other of the plurality of peak chromatograms producing a correlation matrix, each element of said correlation matrix including a correlation value and having associated row and column identifiers identifying which peak chromatogram in said input dataset are associated with said correlation value;

means for clustering said correlation matrix identifying at least one group and at least one row of said correlation matrix as being in said at least one group, each group representing co-varying peak chromatograms;

means for selecting at least one time period of interest for each group; and means for producing a resultant spectrum for each group by sampling extracted ion chromatograms included in each of said groups at each of said at least one time period of interest from said input dataset.

\* \* \* \* \*